(12) United States Patent
Gill

(10) Patent No.: US 9,345,861 B2
(45) Date of Patent: May 24, 2016

(54) DEVICES AND METHODS FOR VASCULAR ACCESS

(71) Applicant: Sukhjit Gill, Oakbrook, IL (US)

(72) Inventor: Sukhjit Gill, Oakbrook, IL (US)

(73) Assignee: Sukhjit Gill, Oakbrook, IL (US)

( * ) Notice: Subject to any disclaimer, the term of this patent is extended or adjusted under 35 U.S.C. 154(b) by 0 days.

(21) Appl. No.: 14/515,748

(22) Filed: Oct. 16, 2014

(65) Prior Publication Data

US 2015/0141958 A1    May 21, 2015

Related U.S. Application Data

(60) Provisional application No. 61/891,822, filed on Oct. 16, 2013.

(51) Int. Cl.
*A61M 5/32* (2006.01)
*A61M 25/06* (2006.01)
*A61M 29/00* (2006.01)

(52) U.S. Cl.
CPC ........... *A61M 25/0606* (2013.01); *A61M 29/00* (2013.01)

(58) Field of Classification Search
CPC . A61M 25/0606; A61M 29/00; A61M 5/158; A61M 25/065; A61M 5/3286
USPC .............................. 604/272, 164.06, 46, 264, 604/164.01–164.05, 164.08, 164.1, 171, 604/273, 274
See application file for complete search history.

(56) References Cited

U.S. PATENT DOCUMENTS

| | | | | |
|---|---|---|---|---|
| 2,904,045 A * | 9/1959 | Owings | ............... | A61M 5/3286 604/274 |
| 3,216,616 A * | 11/1965 | Blankenship, Jr. | ...................... | A61M 5/31596 222/386 |
| 3,540,447 A * | 11/1970 | Howe | .................. | A61B 17/3401 604/165.02 |
| 4,335,718 A * | 6/1982 | Calabrese | ............. | A61M 5/158 604/272 |
| 4,767,407 A * | 8/1988 | Foran | ................... | A61M 25/065 604/117 |
| 5,478,328 A * | 12/1995 | Silverman | ............... | A61M 5/32 604/110 |

* cited by examiner

*Primary Examiner* — Manuel Mendez
(74) *Attorney, Agent, or Firm* — Convergence Intellectual Property Law P.C.; Jonathan Garfinkel

(57) ABSTRACT

A vascular access needle assembly is disclosed. The needle assembly contains a needle and a sheath. The needle has a first part, a second part, and a third part. The needle contains a pointed end configured to penetrate skin of a patient and a sheath slidably and rotatably coupled with the needle. The sheath having one or more irrigation slots configured to transmit a fluid from a fluid source to a vascular region.

17 Claims, 5 Drawing Sheets

DEVICES AND METHODS FOR VASCULAR ACCESS

CROSS-REFERENCES TO RELATED APPLICATIONS

This application claims the benefit and priority of U.S. Provisional Application No. 61/891,822, entitled "Vascular Access Needle Assembly", filed on Oct. 16, 2013, the full disclosure of the above referenced application is incorporated herein by reference.

BACKGROUND

The present disclosure relates generally to the field of medical devices. More specifically, the present invention relates to the field of intravenous medical systems.

Intravenous catheter systems are used in the field of administering medical care. While typical needles and syringes are capable of administering or drawing fluids to and from a patient's blood vessels, an intravenous catheter system allows for multiple or prolonged administrations to or drawings from the patient through the use of a single puncture to a chosen blood vessel.

In a typical IV placement procedure, the medical caregiver prepares the needle entry area by using an antibacterial preparation. Typically, the needle entry area is the skin covering a chosen blood vessel near the surface of the skin. Next, the medical caregiver removes the protective cap from the needle, exposing the needle tip which is protruding from the catheter system. Then, the medical caregiver grasps an area slightly distal to the needle entry area and uses her thumb to anchor the chosen blood vessel.

Next, holding the needle at an angle with respect to the relatively flat needle entry area, the medical caregiver then pierces the patient's skin and tissue over the chosen blood vessel.

Then, the shaft of the needle is lowered toward the patient's skin until it is almost parallel with the skin surface. Thereafter, the needle is advanced into the blood vessel. Then, while holding the retractable needle system steady, the medical caregiver pushes the catheter into the blood vessel by manually sliding the hub portion and catheter away from the retractable needle system along the length of the needle.

Thereafter, the needle retraction system is separated from the catheter system. This causes the needle to be removed from the catheter and the patient. Once the needle is fully removed from the patient, the medical caregiver retracts the needle into the housing by activating the needle retraction mechanism and disposes of retractable needle system. Once the catheter is properly inserted into the blood vessel, additional accessories, including accessories to prevent the spillage of blood, are connected to the hub portion. These accessories allow fluids to be administered or drawn through the IV through various types of needles and devices, including needles, blunts, needleless syringes, IV bags or the like.

Various shortcomings of current IV systems include the difficulty with the initial insertion of the needle into the vessel, especially where the vessel is prone to collapse, and then supporting the vessel once the insertion is completed. At least some of the shortcomings will be overcome by the embodiments described herein.

SUMMARY

Systems and devices for inserting and supporting an intravenous catheter are disclosed.

In one aspect, a vascular access needle assembly as disclosed comprises a needle, wherein the needle has a first part, a second part, and a third part. The needle comprises a pointed end configured to penetrate the skin of a patient and a sheath slidably and/or rotatably coupled with the needle. In one aspect, the sheath having one or more irrigation slots configured to transmit a fluid from a fluid source to a vascular region. In another aspect, a diameter of the first part of the needle is larger than the diameter of the third part of the needle and wherein the diameter of the second part of the sheath decreases such that the second part of the needle assumes a tapered configuration.

In yet another aspect of the vascular access needle assembly, a diameter of the first part of the sheath is larger than the diameter of the third part of the sheath and wherein the diameter of the second part of the sheath decreases such that the second part of the needle assumes a tapered configuration.

In still yet another aspect, the sheath comprises a first part and a second part and may assume a tapered configuration at the distal end.

In another aspect, a method of vascular access by penetrating the skin of a patient comprises advancing a needle through the skin of a patient, wherein the needle comprises a first part, a second part, and a third part and wherein a sheath comprising a first part and a second part is slidably coupled to the needle, advancing the needle in the patient such that the third part of the needle is inserted in a vein and advancing a sheath such that the second part of the sheath is inserted into the vein, de-couple the sheath and the needle and removing the needle from the patient.

Other aspects of the invention include corresponding compositions, methods, and systems are described herein.

BRIEF DESCRIPTION OF THE DRAWINGS

The invention has other advantages and features which will be more readily apparent from the following detailed description of the invention and the appended claims, when taken in conjunction with the accompanying drawings, in which:

DETAILED DESCRIPTION

Figure 1:
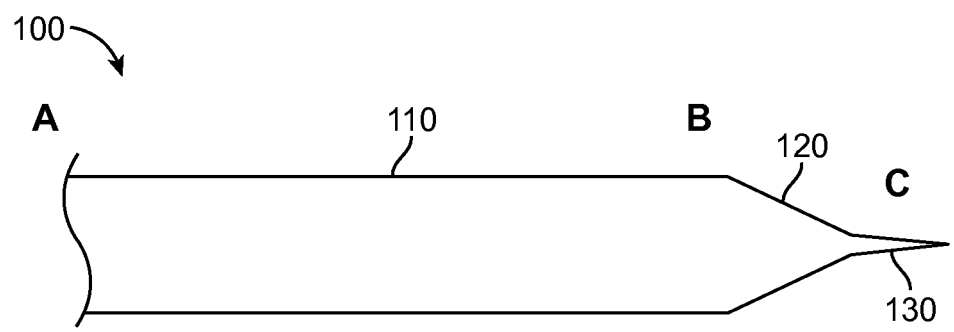
FIG. 1 illustrates one embodiment of a needle of a vascular access needle assembly.

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The word "exemplary" is used herein to mean "serving as an example, instance, or illustration." Any implementation described herein as "exemplary" is not necessarily to be construed as advantageous over other implementations.

As used herein, "proximal" describes a location on the invention that is near or toward the patient's skin as the invention is in operation. Conversely, "distal" describes a location on the invention that is farther or away from the patient's skin than a proximal location as the invention is in operation.

The present disclosure describes devices, systems, and kits of a vascular access needle assembly and methods for vascular access by penetrating the skin of a patient using embodiments of the vascular access needle assembly described herein.

Embodiments of vascular access needle assembly are configured for easy placement of an IV catheter. In one asepct, embodiments of vascular access needle assembly are configured to takes advantage of the ease of inserting a needle, such as a needle in a "butterfly" configuration, into a vein and the advantage of setting up a catheter to facilitate fluid flow.

Embodiments described herein are configured for easy penetration of intravenous needles through skin by using an improved needle and sheath design as described herein. In one aspect, needle with covering sheath is configured for insertion into small veins. In another aspect, one embodiment of needle tip is profiled specially into tapering width and elongated sections extending beyond an elliptical section. In another aspect, the sheath has pointed design to enable advancement. In yet another aspect, the sheath has holes on the sides to improve fluid flow.

Referring now to FIG. 1, where one embodiment of a needle component of a vascular access needle assembly is exemplarily shown. As seen in FIG. 1, the needle 100 comprises a first part 110 (section A-B), a second part 120 (section B-C), and a third part 130 (section C-D). In one embodiment, the third part 130 of the needle component forming the distal tip may be configured as a pointed end to facilitate skin penetration.

In one embodiment, a diameter of the first part 110 of the needle 100 is larger than the diameter of the third part 130 of the needle 100 and wherein the diameter of the second part 120 of the needle 100 decreases such that the second part 120 of the needle 100 assumes a tapered configuration. In one embodiment and as seen in FIG. 1, the diameter of a portion of the needle 100 between the third part 130 and the second part 120 may be substantially the same. In this embodiment, the third part 130 and the second part 120 form an extension or protrusion with respect to the first part 110. Also as seen in FIG. 1, the first part 110 may also be configured with substantially the same diameter. In one embodiment, the diameter of the first part 110 is larger than the diameter of third part 130. The second part 120 is configured with a tapered configuration where a diameter of the proximal end of the second part 120 is configured as the same size as the diameter of the first part 110, and a diameter of the distal end of the second part 120 is configured as the same size as the diameter of the third part 130, wherein the second part 120 transitions the diameter from the first part 110 to the third part 130.

The three part configuration as seen in FIG. 1 may be advantageous where the third part 130 is configured to facilitate vessel penetration. The profile of the first part 110 may be configured to connect the needle 100 to various standard catheters, syringes, or the like. In general, the larger profile enables easy manipulation of the needle 100 during the insertion procedure. The smaller profile of the third part 130 facilitates vessel penetration and enables penetration of small veins. In one embodiment, the needle may be hollow or comprises a lumen disposed within enabling fluid extraction or delivery through the needle.

Figure 2:
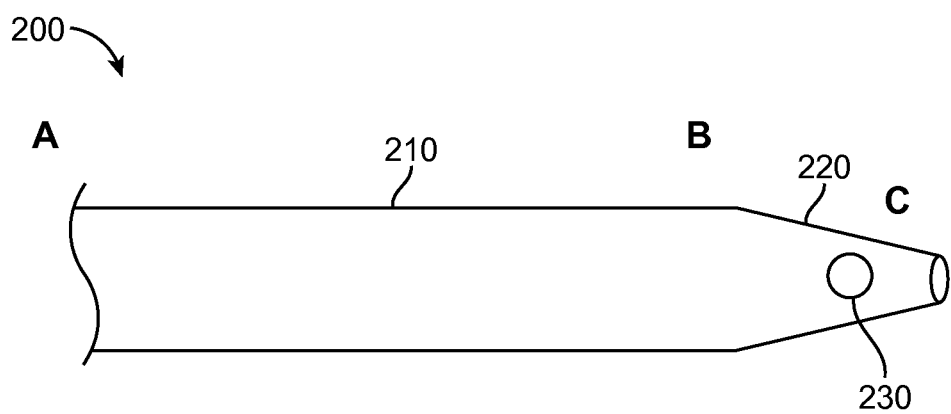
FIG. 2 illustrates one embodiment of a sheath of a vascular access needle assembly.

Referring now to FIG. 2, where one embodiment of a sheath component of a vascular access needle assembly is exemplarily shown. As seen in FIG. 2, the sheath 200 comprises a first part 210 (section A-B) and a second part 220 (section B-C). The sheath 200 is configured to be slidably and/or rotatably coupled with the needle component 100. In one embodiment, when the sheath and the needle are engaged, such as prior to the IV procedure, the third part 130 of the needle 100 is configured to be inserted into an opening of the second part 220, such that the third part 130 of the needle 100 emerges from the sheath 200.

In one embodiment, the first part 210 of the sheath 200 may be configured with substantially the same diameter as the second part 220. In another embodiment, the diameter of the first part 210 is larger than the diameter of second part 220. The second part 220 is configured with a tapered configuration where a diameter of the proximal end of the second part 220 is configured as the same size as the diameter of the first part 210, wherein the second part 220 transitions the diameter from the first part 210 to a smaller diameter as defined by the distal opening of the sheath 200.

The configuration as seen in FIG. 2 may be advantageous where the second part 220 of the sheath 200 is configured to facilitate vessel penetration, especially in an embodiment where the profile of the second part 220 is configured in relation with the profile of the second part of the needle 100. The profile of the first part 210 may be configured to connect the sheath 200 to various standard catheters, syringes, catheter hubs, or the like. In general, the larger profile enables easy manipulation of the sheath 200 during the insertion procedure. The smaller profile of the second part 220 of the sheath 200 enables penetration of small veins, especially as guided by the third part 130 of the needle 100 as described in greater detail below.

Additionally, as seen in FIG. 2, the sheath 200 comprises one or more irrigation slots 230 configured to transmit a fluid from a fluid source to a vascular region. It is noted that since the profile of distal opening of the sheath 200 may be configured to correspond to the profile of the third part 130 of the needle 100. The reduced profile of the distal opening may limit fluid flow, thus, the irrigation slots 230 configured on the side of the sheath 200 enable facilitated penetration while maintaining the rate of fluid communication.

Figure 3:
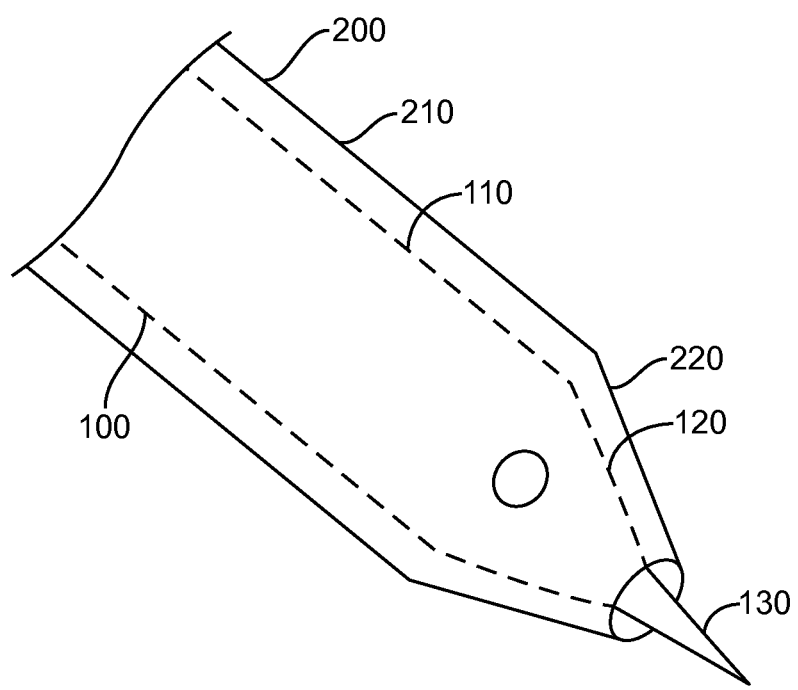
FIG. 3 illustrates one embodiment of a sheath coupled with a needle.

Referring now to FIG. 3, where an embodiment of a vascular access needle assembly where the needle 100 coupled to the sheath 200 is shown. As seen in FIG. 3 the needle 100 comprises a first part 110, a second part 120, and a third part 130. Also, as seen in FIG. 3, the needle 100 is coupled to a sheath 200 which comprises a first part 210 and a second part 220. In one embodiment, and as previously described, the third part 130 of the needle 100 is inserted into an opening of the second part 220 of the sheath 200 when the needle 100 and the sheath 200 are coupled, such that the third part 130 of the needle 100 emerges from the sheath 200.

It is noted that various devices may be connected to the sheath to establish or facilitate fluid or drug administration or fluid retrieval from a patient's blood vessels. For example, a catheter hub with a receptacle which fluidly communicates with the first part of the sheath 210 may be used. The catheter hub may be connected to a fluid source to deliver fluid to the blood vessel.

Figure 4:
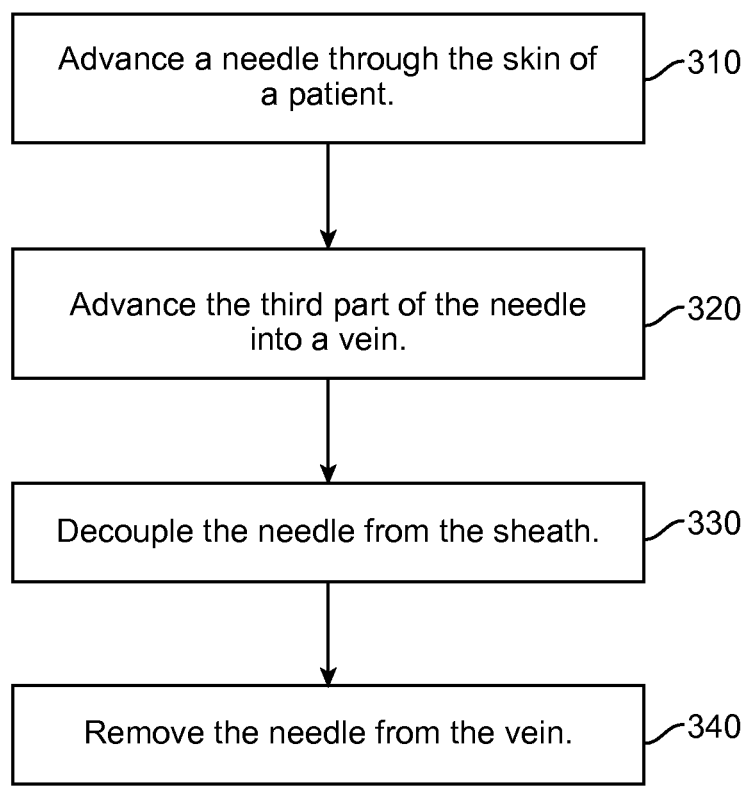
FIG. 4 illustrates a flow diagram of one embodiment of a method of vascular access by penetration through skin of a patient.
Figure 5:
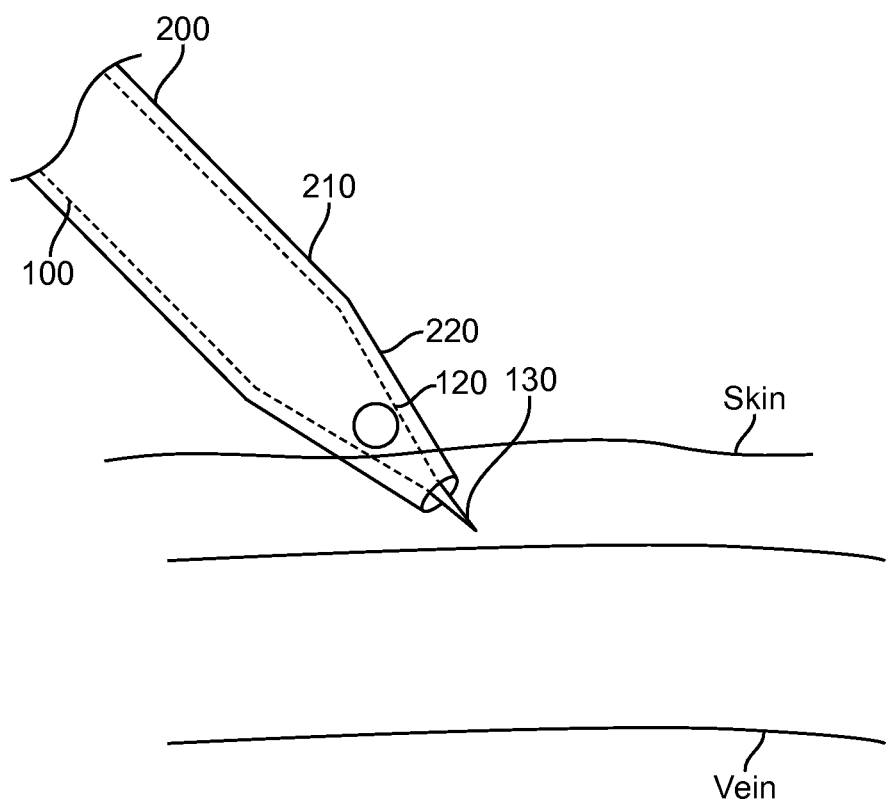
FIG. 5 illustrates one step of a method of vascular access by penetrating the skin of a patient where the needle is inserted into a patient.
Figure 6:
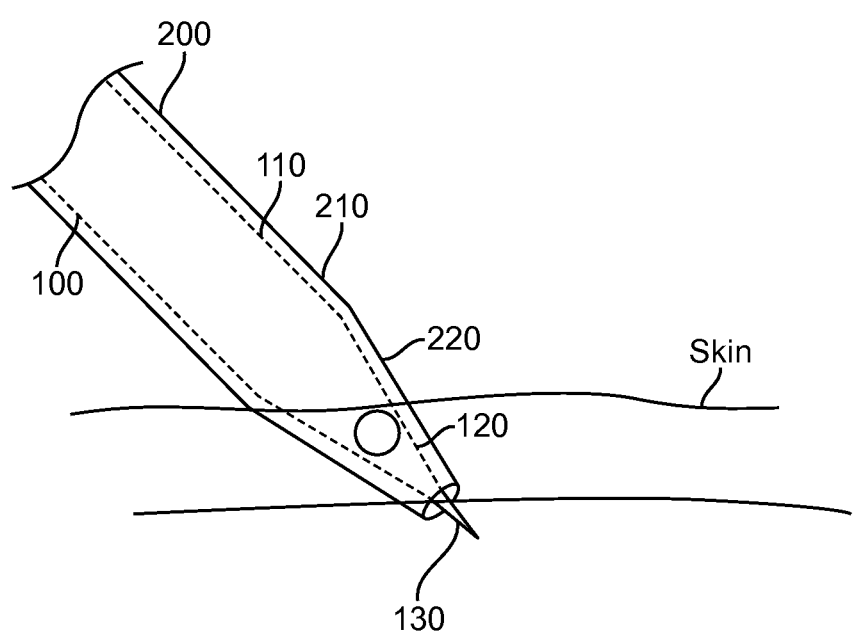
FIG. 6 illustrates another step of a method of vascular access by penetrating the skin of a patient where the sheath is inserted into a patient.
Figure 7:
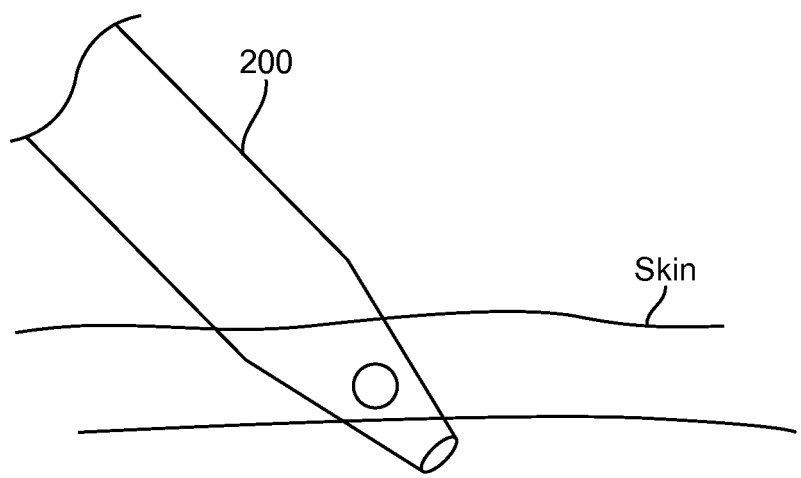
FIG. 7 illustrates another step of a method of vascular access by penetrating the skin of a patient where the needle is retracted from the body and the sheath remains in the patient.

Referring now to FIG. 4, a flow diagram of one embodiment of a method of vascular access by penetration through skin of a patient is exemplarily shown. The steps as illustrated in the FIG. 3 are also shown in FIGS. 5-7. At step 310, a method of vascular access by penetrating the skin of a patient comprises advancing a needle 100 through the skin of a patient. In one embodiment, the needle 100 is held at a 45° degree angle relative to a target surface of the skin. It is noted that the target surface of the skin may be treated to by using an antibacterial preparation prior to the penetration step. In one embodiment, as seen in FIG. 5, the needle 100 comprises a first part 110, a second part 120, and a third part 130. Also, as seen in FIG. 5, the needle 100 is coupled to a sheath 200 which comprises a first part 210 and a second part 220.

As seen in FIG. 5, a third part 130 of the needle 100 is first inserted through the skin of a patient. The small profile of the third part 130 of the needle 100 facilitates the initial insertion, especially for small veins that may be difficult to isolate.

At step 320, and as seen in FIG. 6, the needle 100 is advanced into the patient such that the third part 130 of the needle 100 is inserted into a vein. Thereafter, the second part 120 of the needle 100 is inserted into a vein. Contemporaneously or near contemporaneously, the second part 220 of the sheath 200 is also inserted into the vein. Thereafter, a portion of the first part 110 of the needle 100 is advanced into the vein along with a portion of the first part 210 of the sheath. At step 330, the needle 100 is decoupled from the sheath 200. Thereafter, at step 340 and as seen in FIG. 7, the needle 100 is removed from the vein of the patient while the sheath 200 is placed in a vein and thus establishing an access channel for intravenous fluid delivery or collection.

Figure 8:
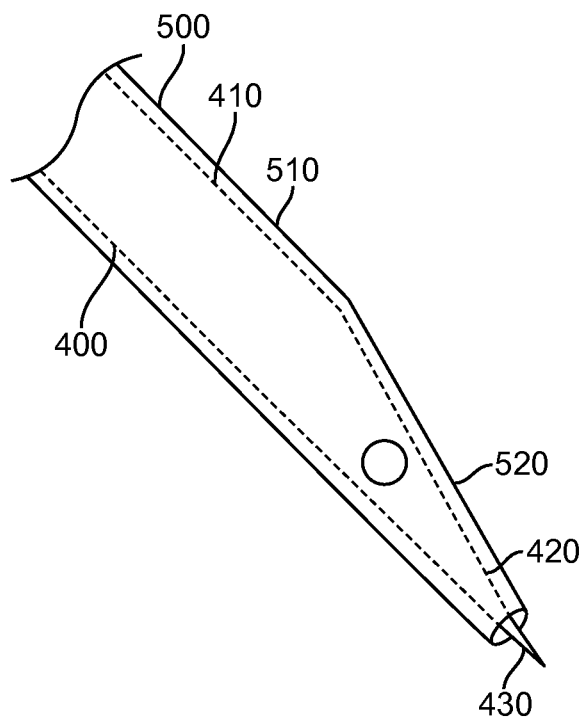
FIG. 8 shows an alternative embodiment of a needle and a sheath of a vascular access needle assembly.

Referring now to FIG. 8, an alternative embodiment of vascular access needle assembly is shown. As seen in FIG. 8, the needle 400 comprises a first part 410 and a beveled second part 420 where the diameter of the second part 420 decreases towards the distal end of the needle. Similarly, the sheath 500 may assume a corresponding configuration where the first part 510 configured to correspond to the first part 410 of the needle and the second part 520 of the sheath is configured to correspond to a portion of the second part 420 of the needle.

The components of the presently disclosed vascular access needle assembly may be formed from a variety of different materials known in the art. For example, the sheath may be fabricated from polyurethanes or silicone and the needle may be fabricated from stainless steel, titanium, as well as from polymers. Additionally, other materials of composition are envisioned.

Also provided herein are kits for use in practicing the subject systems, devices, and methods, where the kits typically include one or more of the above vascular access needle assemblies, as described above, along with other devices such as a fluid source, catheter hub, or the like.

In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate. While the above is a complete description of the preferred embodiments of the invention, various alternatives, modifications, and equivalents may be used. Therefore, the above description should not be taken as limiting the scope of the invention which is defined by the appended claims.

What is claimed is:

1. A vascular access needle assembly, comprising:
    a needle comprising a cylindrical first part, a conical third part, and a tapered second part therebetween, wherein the conical third part of the needle comprises a proximal end having a diameter and a pointed distal end configured to penetrate skin of a patient, such that the third part of the needle assumes a right circular conical configuration; and
    a sheath slidably and rotatably coupled with the needle, the sheath having one or more irrigation slots configured to transmit a fluid from a fluid source to a vascular region;
    wherein a diameter of the cylindrical first part of the needle is larger than the diameter of the proximal end of the third part of the needle and wherein the diameter of the second part of the needle decreases such that the second part of the needle assumes a tapered configuration; and
    wherein the needle is solid along its entire length.

2. The vascular access needle assembly of claim 1, wherein the conical third part of the needle is shorter than the tapered second part of the needle.

3. The vascular access needle assembly of claim 1, wherein the sheath comprises a cylindrical first part, a tapered second part, and a distal opening.

4. The vascular access needle assembly of claim 3, wherein a diameter of the first part of the sheath is larger than the diameter of the second part of the sheath and wherein the diameter of the second part of the sheath decreases such that the second part of the sheath assumes a tapered configuration.

5. The vascular access needle assembly of claim 4, wherein the sheath and the needle are sized such that the conical third part of the needle extends outside of the distal opening of the sheath, the tapered second part of the needle is held within the tapered second part of the sheath, and the cylindrical first part of the needle is held within the cylindrical first part of the sheath when the sheath and the needle are coupled.

6. The vascular access needle assembly of claim 1, wherein the needle further comprises a longitudinal axis; wherein the needle forms an obtuse angle towards the longitudinal axis between the cylindrical first section and the tapered second section; and wherein the needle forms a reflex angle towards the longitudinal axis between the tapered second section and conical third section.

7. A method of vascular access by penetration through skin of a patient, comprising:
    (a) advancing a needle through the skin of a patient, wherein the needle comprises a cylindrical first part, a conical third part, and a tapered second part therebetween and wherein a sheath comprising a cylindrical first part and a tapered second part is slidably coupled to the needle;

(b) advancing the needle into the patient such that the conical third part of the needle is inserted in a vein;

(c) advancing the sheath such that the tapered second part of the sheath is inserted into the vein;

(d) de-coupling the sheath and the needle;

(e) removing the needle from the patient; and (f) delivering fluid directly through the sheath from a fluid source to the vein after the needle has been removed.

8. The method of claim 7, wherein a diameter of the cylindrical first part of the needle is larger than a diameter of a proximal end of the conical third part of the needle and wherein the diameter of the second part of the needle decreases such that the second part of the needle assumes a tapered configuration.

9. The method of claim 8, wherein the third part of the needle assumes a right circular conical configuration.

10. The method of claim 7, wherein the sheath comprises one or more irrigation slots configured to transmit the fluid from the fluid source to the vein.

11. The method of claim 10, wherein the fluid is delivered through the one or more irrigation slots.

12. The method of claim 7, wherein the sheath further comprises a distal opening and wherein the sheath and the needle are sized such that the conical third part of the needle extends outside of the distal opening of the sheath, the tapered second part of the needle is held within the tapered second part of the sheath, and the cylindrical first part of the needle is held within the cylindrical first part of the sheath when the sheath and the needle are coupled.

13. A method of vascular access by penetration through skin of a patient, comprising:

(a) advancing a needle through the skin of a patient, wherein the needle comprises a cylindrical first part, a conical third part, and a tapered second part therebetween and the needle is solid along its entire length, and wherein a sheath comprising a cylindrical first part and a tapered second part is slidably coupled to the needle;

(b) advancing the needle in the patient such that the conical third part of the needle is inserted into a vein;

(c) advancing the sheath such that the tapered second part of the sheath is inserted into the vein; and (d) delivering fluid through the sheath from a fluid source to the vein, wherein the fluid is delivered directly through the sheath from a proximal end of the sheath to an irrigation slot on the tapered second part of the sheath.

14. The method of claim 13, wherein a diameter of the cylindrical first part of the needle is larger than a diameter of a proximal end of the conical third part of the needle and wherein the diameter of the second part of the needle decreases such that the second part of the needle assumes a tapered configuration.

15. The method of claim 14, wherein a diameter of the first part of the sheath is larger than the diameter of the second part of the sheath and wherein the diameter of the second part of the sheath decreases such that the second part of the sheath assumes a tapered configuration.

16. The method of claim 14, wherein the third part of the needle assumes a right circular conical configuration.

17. The method of claim 13, wherein the sheath further comprises a distal opening and wherein the sheath and the needle are sized such that the conical third part of the needle extends outside of the distal opening of the sheath, the tapered second part of the needle is held within the tapered second part of the sheath, and the cylindrical first part of the needle is held within the cylindrical first part of the sheath when the sheath and the needle are coupled.

* * * * *